US008401258B2

(12) United States Patent
Hargrove et al.

(10) Patent No.: US 8,401,258 B2
(45) Date of Patent: Mar. 19, 2013

(54) METHOD TO PROVIDE AUTOMATED QUALITY FEEDBACK TO IMAGING DEVICES TO ACHIEVE STANDARDIZED IMAGING DATA

(75) Inventors: John Hargrove, Honolulu, HI (US); Jia Gu, Honolulu, HI (US); Wenjing Li, Honolulu, HI (US); Rolf Holger Wolters, Kailua, HI (US)

(73) Assignee: STI Medical Systems, LLC, La Jolla, CA (US)

( * ) Notice: Subject to any disclaimer, the term of this patent is extended or adjusted under 35 U.S.C. 154(b) by 1214 days.

(21) Appl. No.: 12/075,890

(22) Filed: Mar. 14, 2008

(65) Prior Publication Data

US 2008/0226147 A1    Sep. 18, 2008

Related U.S. Application Data

(60) Provisional application No. 60/918,527, filed on Mar. 16, 2007.

(51) Int. Cl.
*G06K 9/03* (2006.01)
*G06K 9/52* (2006.01)

(52) U.S. Cl. .......................................... 382/128; 382/311
(58) Field of Classification Search .................. 382/128, 382/274, 291
See application file for complete search history.

(56) References Cited

U.S. PATENT DOCUMENTS

| | | | |
|---|---|---|---|
| 7,038,820 B1 * | 5/2006 | Kindt et al. ................. | 358/474 |
| 2002/0065468 A1 * | 5/2002 | Utzinger et al. ............. | 600/476 |
| 2003/0223626 A1 * | 12/2003 | Hansen et al. ............... | 382/128 |
| 2007/0223654 A1 * | 9/2007 | Aufrichtig et al. .......... | 378/116 |

* cited by examiner

*Primary Examiner* — Robert Kim
*Assistant Examiner* — Eliza Osenbaugh-Stewart
(74) *Attorney, Agent, or Firm* — Martin E. Hsia

(57) ABSTRACT

Automated image quality assessment algorithms, which perform the functions of locating a region of interest, maximizing the image contrast, and ensuring the region of interest is properly centered in the image. Wherein the region of interest is located by spectral matching filter using a target spectrum obtained from samples of the image itself.

14 Claims, 6 Drawing Sheets

(5 of 6 Drawing Sheet(s) Filed in Color)

FIG. 5(a)
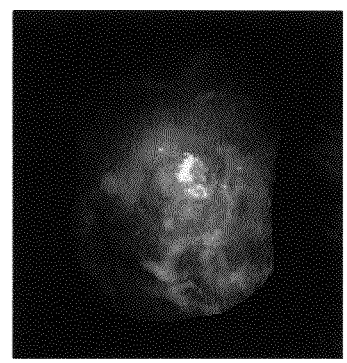
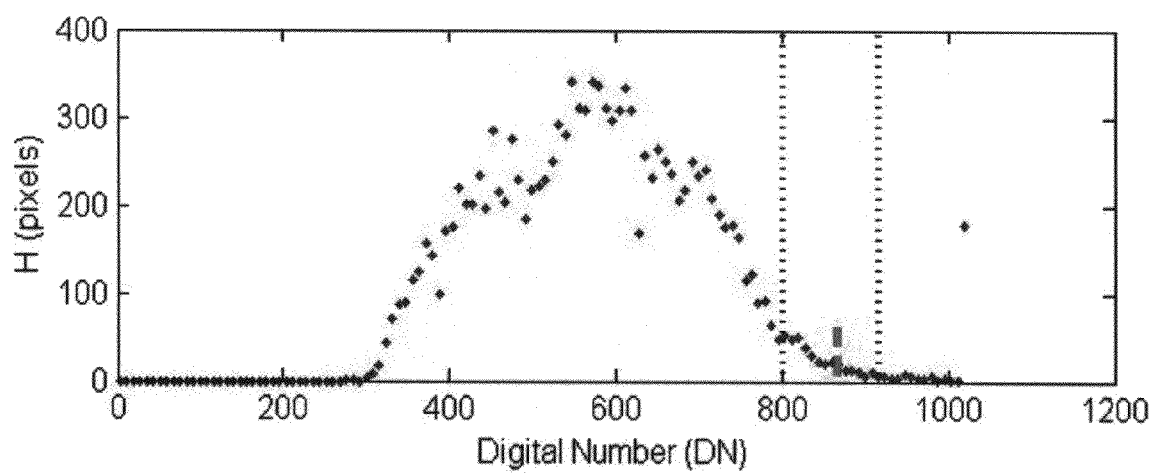
FIG. 5(b)

FIG. 6(a)
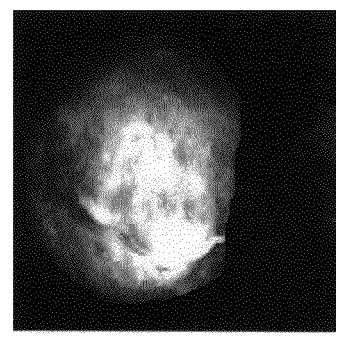
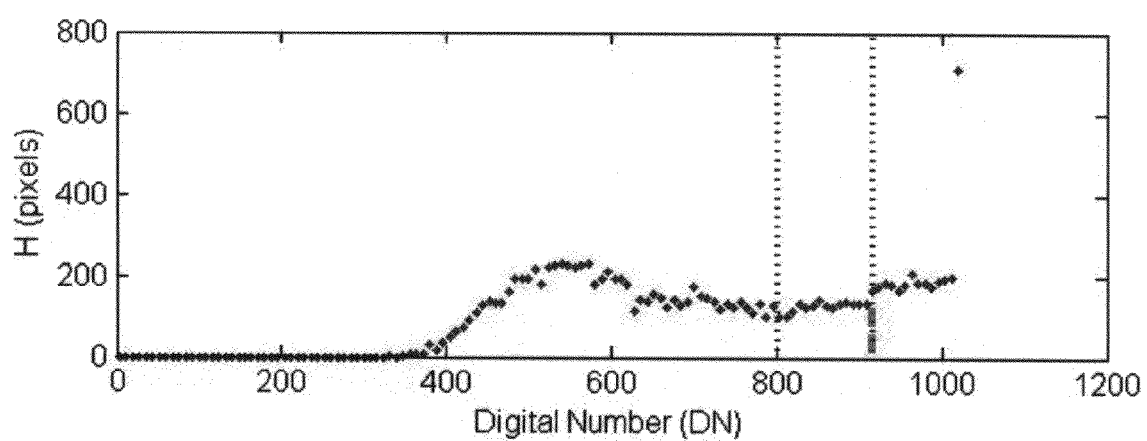
FIG. 6(b)

FIG. 7(a)
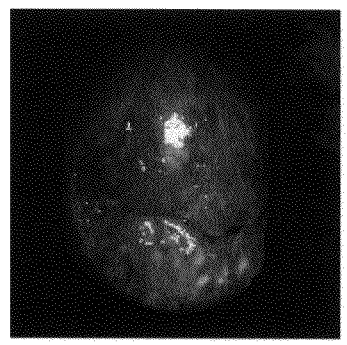
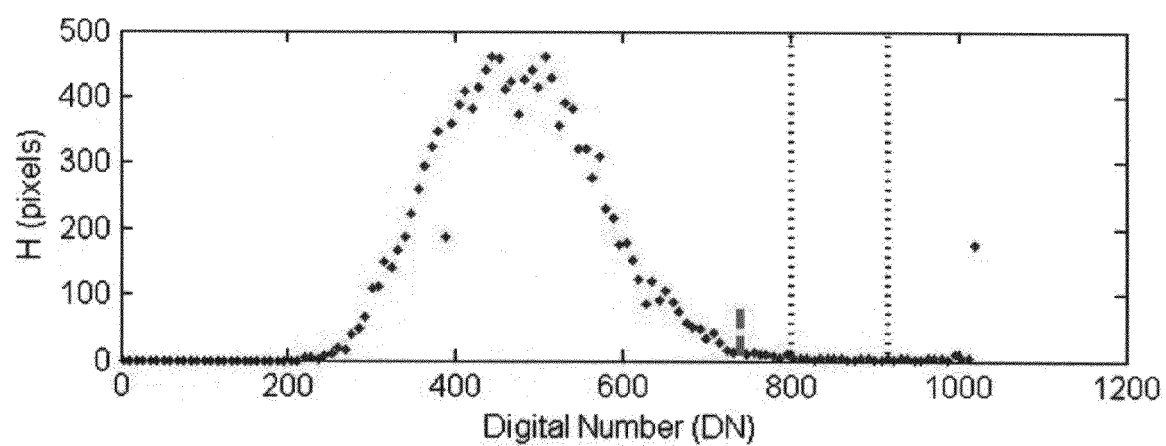
FIG. 7(b).

METHOD TO PROVIDE AUTOMATED QUALITY FEEDBACK TO IMAGING DEVICES TO ACHIEVE STANDARDIZED IMAGING DATA

This continuation-in-part application claims priority to U.S. provisional application 60/918,527 filed on Mar. 16, 2007.

TECHNICAL FIELD

This invention generally relates to medical imaging and more specifically to image processing to achieve high-quality standardized digital imagery to use in archive-quality medical records and Computer-Aided-Diagnosis (CAD) systems. The invention provides a processing system that uses algorithms to analyze the quality of images acquired from a digital imager and produces feedback to actively improve image quality.

BACKGROUND ART

Although this invention is being disclosed in connection with cervical cancer, it is applicable to many other areas of medicine. Uterine cervical cancer is the second most common cancer in women worldwide, with nearly 500,000 new cases and over 270,000 deaths annually (http://wwwdepdb.iarc.fr/globocan2002.htm, incorporated herein by reference). Colposcopy is a diagnostic method used to detect cancer precursors and cancer of the uterine cervix (B. S. Apgar, Brotzman, G. L. and Spitzer, M., Colposcopy: Principles and Practice, W.B. Saunders Company: Philadelphia, 2002, incorporated herein by reference). Scoring schemes such as Reid's index are an aid for making colposcopic diagnoses (Reid R, Scalzi P. Genital warts and cervical cancer. VII. An improved colposcopic index for differentiating benign papillomaviral infection from high-grade cervical intraepithelial neoplasia. Am J Obstet Gynecol 1985; 153:611-618, incorporated herein by reference) based on various features, including acetowhitening, vessel patterns and lesion margins. These features are individually assessed and scored before the scores of all features are combined to yield a composite score that grades disease severity. However, the quality of the images must be assessed before further analysis, to ensure reliable scoring.

The limited quality of cervical imagery can be attributed to several factors, including: incorrect instrument settings, incorrect instrument positioning, glint, blur due to poor focus, and physical contaminants. Glint (specular reflection) eliminates the color information in affected pixels and can therefore introduce artifacts in feature extraction algorithms. Specular reflection is perfect, mirror-like reflection of light from a surface, in which light from a single incoming direction (a ray) is reflected into a single outgoing direction. A pixel is a single point in a graphic image and is the smallest single element of an image. Each pixel in an image has its own value that correlates to its brightness or intensity. In a color image, each pixel can be described using its hue, saturation, and value (HSV) or hue, saturation, lightness (HSL), but is usually represented instead as the red, green, and blue (RGB) intensities. Hue, saturation, and intensity (HSI) and hue, saturation, and brightness (HSB) are alternative names for HSV and HSL. HSL and HSV can be used to represent colors as points in a cylinder whose central axis ranges from black at the bottom to white at the top with neutral colors between them, where the angle around the axis corresponds to "hue", distance from the axis corresponds to "saturation", and distance along the axis corresponds to "lightness", "value", and "brightness".

CAD for colposcopy represents a new application of medical image processing. The inventors have developed a CAD system that mimics diagnostic methods such as Reid's index in order to assess the severity of cervical abnormalities (Lange H. and Ferris, Daron G.; Computer-Aided-Diagnosis (CAD) for colposcopy; SPIE Medical Imaging 2005; SPIE Proc. 5747, 2005, incorporated herein by reference). In order to reliably assess colposcopic features, the imagery upon which CAD operates must be of high quality. Therefore, the present invention includes a systematic framework of algorithms called Active Image Quality Assessment (AIQA), which include locating a region of interest, contrast maximization, and composition analysis. These algorithms automatically assess cervical images acquired from a digital colposcope. The filtered dataset can then be used for CAD algorithms and archive-quality medical records, and can also be used in telemedicine cervical cancer diagnosis.

The assessment algorithms of the present invention are first applied to low resolution raw images sampled from the live video data stream of a digital colposcope in order to determine when requirements of proper contrast and composition are satisfied. System adjustments are made as needed in response to the feedback from the assessment algorithms. These adjustments may consist of both automatic system adjustments, and manual adjustments made by the operator under instrument guidance. After any adjustments, the assessment algorithms are repeated. After the algorithms indicate that no further adjustments to the system are required, the system is ready to collect high-resolution still images for use in a CAD system.

While many of the assessment algorithms are well-known in the art, the inventors are not aware of any other image processing method that uses a grid box sampling method to estimate the target spectrum that is used by a spectral matched filter to locate a region of interest. The following patents and patent applications may be considered relevant to the field of the present invention:

PCT Application No. WO/2008/012813 to Gal, incorporated herein by reference, discloses a medical device for performing a vaginal examination that comprises an imaging sensor, wide field of view optics, illumination means, electronic circuitry, and communication means. In addition it discloses a medical image and analysis (MIUA) unit comprising a processor and a dedicated MIUA algorithm. The imaging sensor, optics and illumination means gather images at different wavelengths to provide multi-spectral imaging. The imaging device consists of at least one filter. The MIUA algorithm checks the images for the presence of a region of interest and compares the acquired images to a predefined standard of quality and if the acquired images do not meet the predefined standard, adjustments to the illumination intensity, exposure time, angle, and camera zoom can be adjusted. Lastly, the MIUA algorithm verifies that sufficient images of a predefined region of interest have been obtained, and saved, and then signals the user of the same.

U.S. Patent Application Publication No. 2007/0133852 to Collins, Jeffery et al., incorporated herein by reference, discloses a system and method of computer aided analysis of medical images and detection of malignant lesions. Medical images are obtained from multiple modalities and analyzed. Morphological features as well as temporal, i.e., kinetics features, are combined to compute a consolidated assessment of a possible lesion detected in the medical images. The system includes at least one kinetics module, which is capable of extracting kinetics features from a time sequence of MRI images or MRS data taken after administering a contrast enhancement agent to a patient. The consolidated assessment is presented to a user for confirmation or modification.

U.S. Pat. No. 6,766,184 to Utzinger et al., incorporated herein by reference, discloses methods and apparatus for generating multi-spectral images of tissue. The multi-spectral images may be used as a diagnostic tool for conditions such as cervical cancer detection and diagnosis. Primary radiation is produced with an illumination source which is filtered to select a first wavelength and a first polarization. Tissue is illuminated with the filtered primary radiation to generate secondary radiation, which is filtered to select a second wavelength and a second polarization. The filtered secondary radiation is collected with a detector, and a plurality of multi-spectral images of the tissue is generated according to different combinations of first and second wavelengths and first and second polarization with an analysis unit in operable relation with the detector.

U.S. Patent Application Publication No. 2004/0068167 to Hsieh et. al., incorporated herein by reference, discloses a method and system for generating and processing image data based on analysis of an initial image by a computer aided diagnosis algorithm. The CAD algorithm may include modules such as accessing image data, segmenting data or images, feature selection or extraction, classification, training, and visualization. It discloses locating a feature of interest via segmentation or structure identification. It also discloses post-processing techniques that focus on various parameters such as contrast, spatial resolution (e.g. zoom), and color.

U.S. Pat. No. 6,687,329 to Hsieh et al., incorporated herein by reference, discloses a technique for acquiring subsequent image data in a medical diagnostic context based upon analysis of initial image data via a computer aided diagnosis algorithm to determine whether additional image data acquisition is appropriate.

U.S. Patent Application Publication No. 2004/0208385 to Jiang, incorporated herein by reference, discloses methods of enhancing images of tissue samples for diagnostic purposes by filtering luminance values from an input image and transforming the filtered value to produce an enhanced image. The invention uses a transformation algorithm that adjusts for image brightness, contrast, and may provide color balancing. It also discloses a masking technique for regions of a sample that are obstructed or lie outside of a zone of diagnostic interest.

U.S. Pat. No. 6,277,067 to Blair, incorporated herein by reference, discloses a low cost, hand-held colposcopy assembly capable of producing a digital image of the cervix and enables real-time imaging and archiving of cervical images for detecting cancerous tissue. The digital images created may be instantaneously processed to remove reflective glare or to perform any digital image enhancement operations to determine tissue texture, tissue and lesion borders, and tissue vascularity.

U.S. Patent Application Publication No. 2007/0171363 to Chen, Ying-Ling Ann et al., incorporated herein by reference, discloses an adaptive photoscreening system.

U.S. Patent Application Publication No. 2007/0009096 to Cresens and Marc, incorporated herein by reference, a method for canceling the impact of the physical property variability on the image quality performance of a digital imaging system, obtained during quality control (QC) analysis using a serial numbered quality control (QC) target by applying physical property deviation controlled behavior model corrections to the raw image quality performance. The serial numbered QC-target used for the QC analysis comprises target-specific, measured physical property data encoded in- or outside of QC-target.

U.S. Patent Application Publication No. 2007/0237308 to Reiner and Bruce, incorporated herein by reference, discloses a quality assurance system and method that generates a quality assurance (QA) scorecard for technologists that use digital devices in a radiological-based medical imaging study.

U.S. Patent Application Publication No. 2007/0248210 to Selse, Emil et al., incorporated herein by reference, discloses automated quality assessment of a digital mammographic image with respect to the positioning of a patient's breast.

U.S. Pat. No. 6,147,705 to Krauter et al., incorporated herein by reference, discloses an apparatus and method for video colposcope with electronic green filter. A video camera obtains a subject electronic image of a subject object, and using algorithm-driven digital signal processing circuitry (DSP), color saturation, hue, and intensity levels of the subject electronic image are modified according to DSP reference filter algorithm and reference color balance levels as stored, thus producing a modified electronic image corresponding to the subject electronic image. The modified electronic image is outputted to a display in continuous real time as the corresponding subject image is obtained by the video camera. This modified electronic image emulates that obtained through an optical green filter and incorporates a simulated white balance.

U.S. Pat. No. 5,565,678 to Manian, incorporated herein by reference, discloses a system and method for performing a rapid, automatic, quantitative assessment of the image quality of a radiographic image.

DISCLOSURE OF INVENTION

The present invention discloses a method to provide automated quality feedback to imaging devices to achieve standardized imaging data. It comprises the steps of illuminating a field of view with a light source to obtain a cross-polarized (XP) image and singly-polarized (PP) image (sometimes referred to as a parallel-polarized image). The XP image is preferably created by illuminating a field of view with a light source having a first polarization orientation and viewing the field of view with a detector through a polarized filter having a second polarization orientation that is substantially perpendicular to the first orientation. The PP image is preferably created when the first polarization orientation is substantially parallel to the second polarization orientation. It can also be obtained by placing a singly polarized filter at either the light source or the detector (but not both). Both the XP and PP images are co-registered (aligned). A region of interest is then located on the XP image using an image classification algorithm that defines a target spectrum by taking the mean spectrum of spatially dispersed samples of the cross-polarized image, discarding approximately 0-20% of the brightest samples and 10-50% of the darkest samples, and averaging the remaining spectra. The region of interest's size is then determined by matching that portion of the XP image that corresponds to the target spectrum. Next, the region of interest and PP image are analyzed for proper contrast using signal assessment and exposure time adjustment. Composition analysis is then applied to the XP image to ensure the region of interest is properly centered within the image borders. Lastly, an assessment status of contrast maximization and composition analysis is performed and the system reports either a Boolean variable of "good" or "bad". If the status is "bad", then the whole process (collecting two versions of a raw image, locating a region of interest, performing contrast maximization and applying composition analysis) is repeated until an assessment status of "good" is achieved. If the status is "good", meaning that contrast maximization and composition analysis are satisfactory, then the system is ready for the collection of high-resolution still imagery of the region of interest.

BRIEF DESCRIPTION OF DRAWINGS

The patent or application file contains at least one drawing executed in color. Copies of this patent or patent application with color drawing(s) will be provided by the Office upon request and payment of the necessary fee.

FIGS. 5(a) and 5(b). RGB image of cervix masked by ROI (FIG. 5(a)) and histogram of digital number (DN) values for red pixels in the ROI (FIG. 5(b)). The minimum and maximum acceptable values for signal DN are shown as two vertical dashed lines. The line at 860 DN is the value of signal DN estimated by the contrast algorithm. This image has acceptable contrast.

FIGS. 6(a) and 6(b). RGB image of cervix masked by ROI (FIG. 6(a)) and histogram of DN values for red pixels in the ROI (FIG. 6(b)). The minimum and maximum acceptable values for signal DN are shown as two vertical dashed lines. The line at about 900 DN is the value of signal DN estimated by the contrast algorithm. This image is over-exposed.

FIGS. 7(a) and 7(b). RGB image of cervix masked by ROI (FIG. 7(a)) and histogram of DN values for red pixels in the ROI (FIG. 7(b)). The minimum and maximum acceptable values for signal DN are shown as two vertical dashed lines. The line at about 750 DN is the value of signal DN estimated by the contrast algorithm. This image is under-exposed.

BEST MODES FOR CARRYING OUT INVENTION

Before the assessment algorithms of the invention can be performed, low resolution raw images of the field of view must be collected from live video during examination with a digital imager. Two versions of the field of view are captured, an XP image and a PP image. This is preferably achieved by illuminating the field of view with a polarized light source having a first polarization orientation and viewing the field of view with a detector through a polarized filter having a second polarization orientation that is substantially perpendicular to the first polarization orientation. This produces the XP image of the field of view. The second version of the field of view is preferably achieved when the polarized light source has a first polarization orientation that is substantially parallel to the detector filter's second polarization orientation, or when there is only one polarization filter either at the light source or at the detector, to produce a PP image of the field of view.

A broadband white light source (having an almost infinite number of wavelengths) and multi-spectral detection through the use of a standard color sensor with red, green, and blue color channels (i.e. capable of detecting these three wavelengths) are preferably used.

1. The Assessment Algorithm Sequence
1.1 Locating a Region-of-Interest (ROI)

Figure 1:
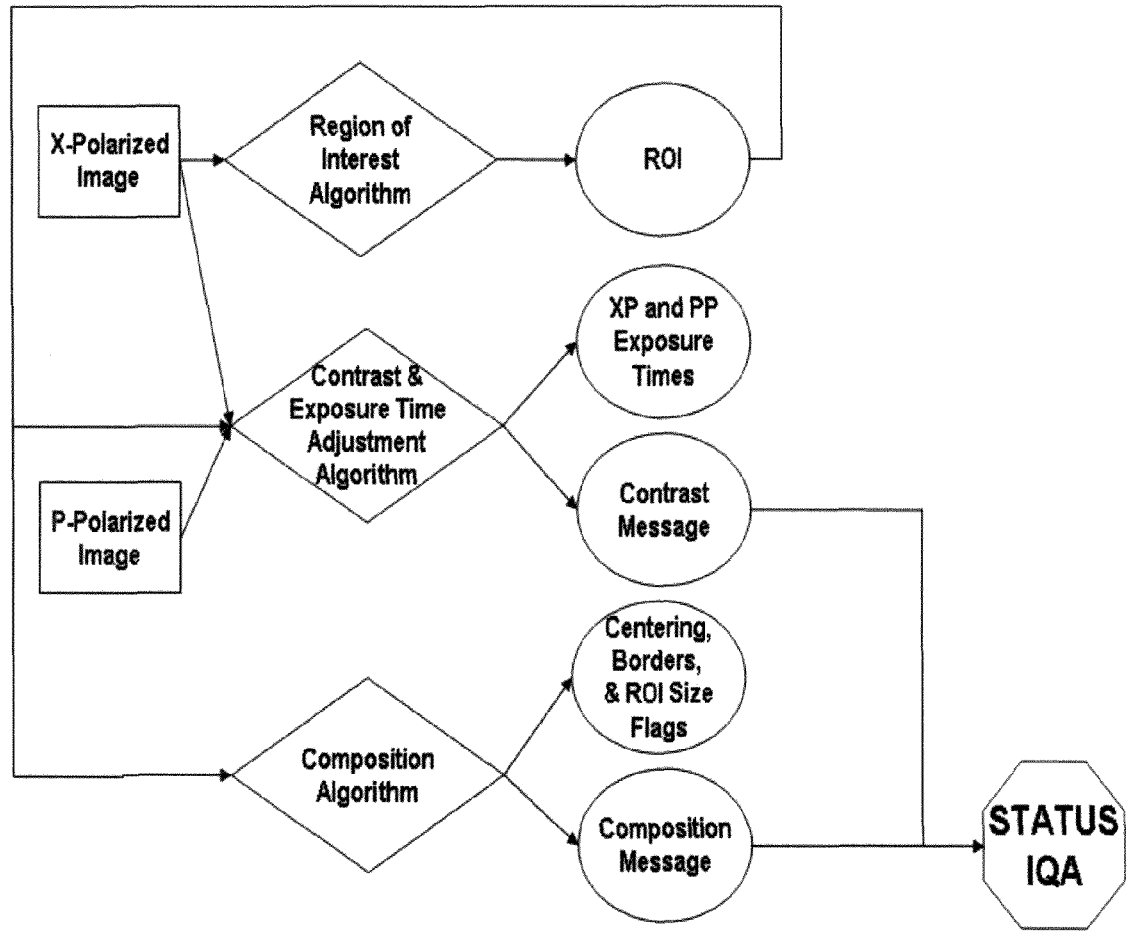
FIG. 1 Flowchart of Active Image Quality Assessment (AIQA).

A flowchart for a presently preferred embodiment of the invention is provided in FIG. 1. The invention assumes that the system has been correctly focused by a focus subsystem. There are preferably three algorithms: (1) region of interest location; (2) contrast maximization; and (3) composition analysis. After these algorithms have been applied, an overall status assessment is performed. The first algorithm is the computation of a region of interest (ROI), which should correspond to the cervix. The ROI is estimated using the XP image because it is not susceptible to glint artifacts (specular reflection). Specular reflection is perfect, mirror-like reflection of light from a surface, in which light from a single incoming direction (a ray) is reflected into a single outgoing direction. The estimated ROI is then used as input for the remaining two algorithms: contrast maximization and composition analysis.

1.2 Contrast Maximization

For this algorithm, the contrasts for the XP and PP images of the field of view are maximized independently. Performing contrast maximization on the PP image is necessary because, due to polarization effects, the two images receive differing amounts of light. As a result, the exposure time must be adjusted for each exposure independently to maximize each image's contrast. Contrast maximization for XP and PP images utilizes the ROI estimate from the XP image as input.

The goal of this portion of invention is to ensure that the dynamic range of the camera is fully utilized, thereby maximizing image contrast. Contrast maximization is achieved through signal assessment and exposure time adjustment. This means the camera exposure times are adjusted so that the brightest cervical pixels (those producing the largest digital numbers (DN) in the raw image) are as close as possible to saturating the camera without doing so. A pixel is a single point in a graphic image and is the smallest single element of an image. Each pixel in a image has its own value that correlates to its brightness or intensity. A numeric representation of zero usually represents black, and the maximum value possible usually represents white. A DN is a positive integer representing the relative brightness of a pixel in a digital image. In a color image, each pixel can be described using its hue, saturation, and value (HSV), but is usually represented instead as the red, green, and blue (RGB) intensities.

The primary output from the contrast maximization algorithm is a message indicating whether the system has achieved satisfactory contrast. If the system has not achieved satisfactory contrast, a new exposure time to apply to a test image is provided, the rest of assessment algorithms are not executed, the sequence terminates for that image, and a new test image with the new exposure time is taken. If, however, acceptable contrast has been achieved, the output exposure times are unchanged, and the assessment algorithms continue on to composition analysis.

1.3 Composition Analysis

Composition analysis is the third stage of the presently preferred embodiment of the invention. The purpose of composition analysis is to ensure that the ROI (preferably the cervix) is centered within each image and fills as much of the field of view as possible, without intersecting the image borders. The ROI from the XP image is used as input. The center of the ROI is calculated and compared to the center of the image. The proximity of the ROI borders to the image borders is assessed. Finally, the size of the ROI is calculated in order to detect cases in which the cervix is obstructed in the camera field of view. If the ROI is centered, the ROI does not intersect the image borders, and the ROI is sufficiently large (constituting at least 25% of the total area of the XP image), then the output composition message indicates that composition is good. If this is not the case, then the composition is bad and is indicated in three quality flag outputs (described below). With this information, a human operator is able to make adjustments to composition.

1.4 Status Assessment

The final stage of the presently preferred embodiment of the invention is the determination of an overall status for the assessment algorithms, which is reported as the Boolean variable of either "good" or "bad". The overall status is assigned the value "good" (true) only when the two assessment algorithms (contrast maximization and composition analysis) are both satisfactory. When the overall status is "good", the system is ready for collection of high-resolution still imagery of the ROI for the observation of clinically relevant features. If any of the two assessment algorithms (contrast maximization and composition analysis) are unsatisfactory, the overall status is "bad" and the whole process (locating a ROI, contrast maximization, composition analysis, and status assessment) is repeated. after system adjustments have been made based on the contrast and composition flags.

2 Locating a Region of Interest

2.1 Problem Description

Figure 2:
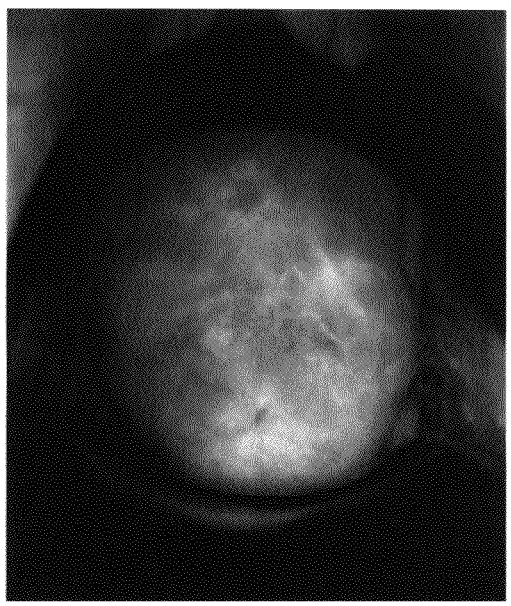
FIG. 2 Example of Red-Green-Blue (RGB) image of cervix, but also including vaginal wall, matte black speculum, and portions of external anatomy.

The purpose of the ROI algorithm is to identify the pixels in the raw image which correspond to the cervix. These pixels are then used to analyze image contrast and composition. An example is shown as FIG. 2, for which the raw image has been converted to a Red-Green-Blue (RGB) image. Although the cervix is clearly visible in the center of the image, several other features are visible in the image such as the vaginal walls, the matte black speculum, and portions of the external anatomy. Only the cervical pixels are of interest for analysis of image quality.

2.2 Algorithm Description

Because the XP and PP images are co-registered (aligned), it is sufficient to calculate the ROI from a single image. If one camera is used (with a time delay between image captures), the time delay must be short enough to minimize tissue movement so the images are co-registered, or else a half silvered mirror splitter beam or other mechanism for simultaneously taking two co-registered images must be used. As stated earlier, the ROI is estimated using the XP image because it is not susceptible to glint artifacts. The raw XP image, which is usually in Bayer pattern format, must first be converted to an RGB image. A Bayer pattern format refers to a particular arrangement of color filters used in most single-chip digital image sensors used in digital cameras to create a color image. The filter pattern is 50% green, 25% red and 25% blue, hence it is also called RGBG. Twice as many green elements as red or blue are used to mimic the human eye's greater sensitivity to green light. To convert this to RGB, a complex demosaicing process is undesirable due to computation burden and associated time delay. Instead, a simple binning is used which is both fast and sufficient for the purpose here. Each RGB pixel is composed of a single red pixel from the raw, a single blue pixel, and the average of the two adjacent green pixels.

The basic mathematical function utilized to calculate the ROI is spectral match filtering. Spectral match filtering works very well and is fast to compute. In telecommunications, a matched filter is obtained by correlating a known signal, or template, with an unknown signal to detect the presence of the template in the unknown signal. Two-dimensional matched filters are commonly used in image processing. The matched filter used in this invention, estimates the spectral angle between a target spectrum corresponding to the cervix and each pixel that is potentially on the cervix. A spectrum is a condition that is not limited to a specific set of values but can vary infinitely within a continuum.

The target spectrum and all samples of spectra can be represented in multi-dimensional space. In this space, the red pixel value of a spectrum corresponds to the value in the red dimension, the green pixel value of a spectrum corresponds to the value in the green dimension, and the blue pixel value of a spectrum corresponds to the value in the blue dimension. The red, green, and blue values together define a vector in this space. The target spectrum and all samples of spectra can be represented as vectors this space. The spectral angle between the target spectrum vector and each sample spectrum vector can be assessed. Pixels for which this angle is less than some minimum threshold are deemed sufficiently similar to the cervical target pixels to pass filtering. Preferably the spectral angle between the target spectrum and the sample spectra should less than approximately 65-85 degrees. Optimally, the angle should be less than approximately 75 degrees. The spectral angle is preferably calculated in the "whitened" RGB space, that is, in the color space which has been rotated and normalized by the color covariance matrix of the pixels (defined below).

To estimate the matched filter, first the sets of bad pixels are defined as all pixels with values that are very close to zero or that are very near saturation. The remaining pixels are hereafter referred to as the background pixels. First, the bad pixels are discarded and the mean (average) spectrum $\mu_{bkg}$ and covariance matrix $\Sigma$ of the background pixels are then calculated. In statistics, the covariance matrix is a matrix of covarinaces between elements of a vector. Covariance is the measure of how much two random variables vary together (as distinct from variance, which measures how much a single variable varies). If two variables tend to vary together (that is, when one of them is above its expected value, then the other variable tends to be above its expected value too), then the covariance between them is positive. On the other hand, if when one of them is above its expected value, and the other variable tends to be below its expected value, then the covariance between the two variables will be negative.

Next, a target spectrum corresponding to the cervix is generated. This is achieved by using a grid box sampling method which includes taking spatially dispersed samples of spectra within the ROI in the XP image. This method of locating the ROI is desirable because the traditional problem with spectral matched filters is obtaining the "target spectrum" to compare to or "match" to the image pixels. The inherent spectrum characterizing the cervix will always vary for different women due to natural variability. It is preferable to obtain the target spectrum from the image itself, but the problem remains how to obtain a cervical target spectrum from the image itself when the purpose of the ROI algorithm is to find the cervix in that image. The grid box method addresses this problem through sampling.

Figure 3:
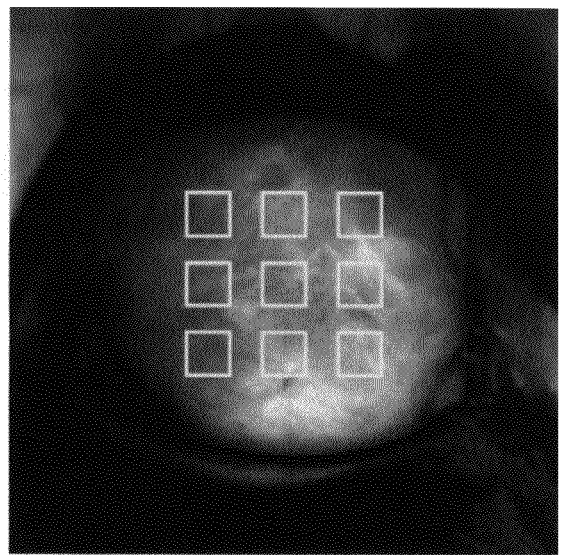
FIG. 3 RGB image of cervix with nine boxes used to estimate target spectrum for spectral matched filter.

FIG. 3. shows nine spaced apart boxes (samples) of pixels. The size of the boxes and spacing between them are adjustable. Preferably, but not necessarily, the boxes are of uniform size and uniform spacing wherein the box lengths are approximately 10-30% of the border length of the XP image, and the boxes cover approximately 20-60% of the total area of the XP image. The boxes need not be square but can be any desired shape. The mean spectrum of each box is calculated. Optimally, approximately 12% of the spectra from the brightest (highest DNs) and 30% of the darkest (lowest DNs) boxes are then discarded and the remaining spectra are averaged to produce the target spectrum $\mu_{trg}$. However, the target spectrum is operable if approximately 0-20% of the brightest and approximately 10-50% darkest samples are discarded.

A filter value, preferably the cosine of spectral angle (preferably in whitened space), is then calculated for each background pixel A preferably using the following equation:

$$f(A) = \frac{(\mu_{trg} - \mu_{bkg})' \sum^{-1} (A - \mu_{bkg})}{\sqrt{(\mu_{trg} - \mu_{bkg})' \sum^{-1} (\mu_{trg} - \mu_{bkg})} \sqrt{(A - \mu_{bkg})' \sum^{-1} (A - \mu_{bkg})}}. \quad (1)$$

This filter value is used to determine whether a pixel is filtered out or retained.

A two-dimensional matrix with the same number of pixels as the RGB image is initialized with zeros. The filter value for each background pixel is written to this matrix. The value for bad pixels is left as zero. If the angular threshold of 75 degrees is chosen, this corresponds to a filter value $f(A)=\cos(75)=0.259$. A second two-dimensional matrix of zeros is initialized. For pixels with a filter value $f(A)>0.259$, the matrix is assigned a value of one. The result of the above is two matrices, one with the filter value for each background pixel and zero for each bad pixel, and the second with a value of one for each pixel that has a high enough filter value and zero for all other pixels.

Figure 4:
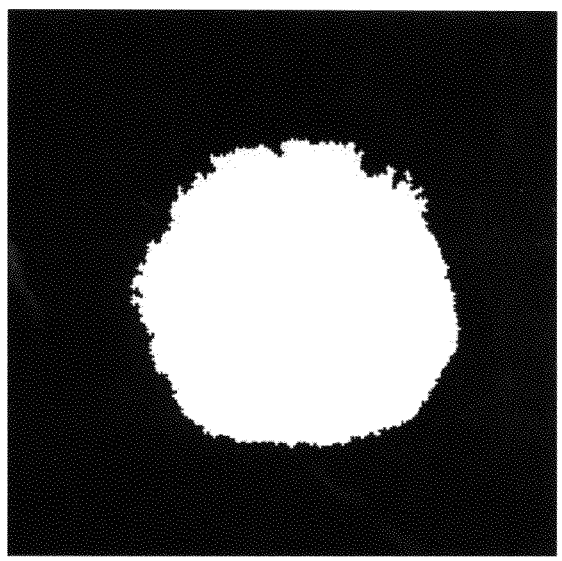
FIG. 4 Cervical Region of Interest (ROI) for image in FIG. 4 and FIG. 5 calculated using AIQA ROI algorithm.

This matrix then undergoes morphological operations to further refine the cervical ROI. "Blobs" or clusters of contiguous pixels are identified. Contiguous pixels are defined as those sharing sides, while pixels touching at the corners are not defined as contiguous. The area of each blob is calculated and then all but the largest blobs are eliminated. The result is the ROI. An example is shown as FIG. 4. Finally, the number of pixels in the ROI is counted.

3. Contrast Maximization
3.1 Problem Description

Contrast is a measure of the gradation (difference) in luminance (brightness) that provides information. It is expressed as the ratio (difference in luminance)/(average luminance) in adjoining portions of a field of view. Generally speaking, contrast is the smallest difference two nearby signals can have and still be distinguishable. Under optimum conditions, the human eye can detect the presence of 2% contrast. Therefore, in order to discern the same clinically relevant features observed by an expert colposcopist in imagery produced by the digital colposcope, the device must be capable of detecting a contrast of at least 2%. As a goal, the device will be capable of detecting contrast of less than 2%.

Contrast is defined as $$\text{contrast} = \frac{\sigma_{dark}}{signalDN - \mu_{dark}}. \quad (2)$$

The numerator is the standard deviation of the dark noise. This is obtained from the "dark file" during the device characterization procedure (the procedure which characterizes or measures the instrument in terms of noise, dynamic range, signal to noise, output power, etc.). The denominator is the signal intensity from which the mean of the dark file (essentially the zero-signal point of the camera) is subtracted. The justification for defining contrast as above is that the minimum difference in luminosity which can be detected by the system is equal to the system noise (estimated from the dark noise), while the average luminosity for two signals of very nearly the same amplitude is approximately the amplitude of one of the signals. If the signal DN registered for a given signal luminance is increased by elevating the gain in an analog to digital converter, the dark noise will be amplified as well, resulting in no improvement in contrast. As stated earlier, a digital number (DN) is a positive integer representing the brightness of a pixel in a digital image. Poor contrast is more likely the result of insufficient light-source intensity or a too-short camera exposure time. Increasing the light-source intensity will increase signal DN without changing dark noise. In this case, in equation (2) the numerator stays fixed while the denominator increases, thereby lowering (improving) contrast. However, the design of the digital colposcope normally dictates that the intensity of the light source remains fixed. As a result, lengthening the exposure time is usually the only available method for improving contrast.

Of course, if the exposure time is too long, then cervical pixels may become saturated either by overflowing the camera's photon wells or its analog to digital converter. When this happens, information is destroyed for those pixels and the inherent luminance of the cervix cannot be measured. In fact, information may be corrupted before the saturation point because the response of the camera becomes non-linear as it nears saturation. Therefore, it is desirable to limit the brightest signals to some maximum DN slightly less than saturation. This value should also be obtained from the device characterization procedure.

Glint pixels are those whose signal DN is abnormally high (relative to the rest of the image) because of specular reflection of the light source. As stated earlier, specular reflection is perfect, mirror-like reflection of light from a surface, in which light from a single incoming direction (a ray) is reflected into a single outgoing direction. At least a few glint pixels are likely to be encountered in nearly all images by polarization obtained with the PP camera (glint pixels are suppressed in the XP camera). Assuming their number is few, glint pixels should not be used to characterize contrast because they do not represent the signal DN of the cervical pixels.

The purpose of the contrast maximization algorithm is to ensure that imagery collected for the observation of clinically relevant features exhibits the best possible contrast. Because the camera noise is essentially fixed, the best possible contrast is achieved by determining the exposure time, preferably from a pre-defined list which produces the highest value of signal DN for the brightest cervical pixels, but still is less than the onset of the non-linear range or saturation.

3.2 Algorithm Description

The contrast maximization algorithm has two main parts. The first part is signal assessment. The purpose of signal assessment is to estimate signal DN for the brightest cervical pixels. The second part is exposure time adjustment, which adjusts the exposure time based on the value of signal DN, if necessary. The contrast maximization algorithm utilizes contrast stretching (often called normalization) which involves expanding a measured range of digital numbers in an image to a larger range, to improve the contrast of the image and its component parts. The "stretching" is achieved by the adjusting the exposure time to get a larger number of pixels at a higher DN value (closer to the saturation point).

The reflectance of the cervix is highest in the optical spectrum range corresponding to red. As a result, the signal DN for the cervix is always highest in the red band of the image. The algorithm therefore only uses the red band (if, for example, the signal DN in the blue band were maximized, the red band would probably be saturated). The algorithm then eliminates all pixels in the red band that are not within the region of interest. A histogram of the remaining pixels is then calculated. Of course, for other applications, different spectral bands could be used.

The algorithm accepts as inputs the maximum and minimum acceptable values for signal DN. Both the XP and PP image are assessed. Preferably, the minimum acceptable value corresponds to approximately 80% to 90% of the maximum DN value for the image. For 8 bit images, DN values lie in the range 0-255. For our invention we use 10 bit images with DN values within the range of 0-1023.

Beginning at the maximum acceptable value, the algorithm analyzes the shape of the histogram looking for an "edge", where the number of pixels within a certain range of DN begins to increase sharply. An example for a PP image is given as FIG. 5(a).

In FIG. 5(b), there are almost 200 saturated pixels for this image (DN=1023) according to the histogram. However, these are ignored in the search for the histogram edge. The histogram values (or "histogram bins") to the immediate left of the saturation value (or "saturation bins") have a very small number of pixels. The histogram then begins to curve upward, characterizing the brightest cervical pixels. Maximum signal DN for this image, 860, is midway between the minimum acceptable value of 800 and the maximum acceptable value of 920. Again, the minimum acceptable value and maximum acceptable value correspond to approximately 80% (800) of the maximum value of DN available for the image (1023) and 90% (920) of the maximum value of the DN available for the image (1023). As a result, the image in FIG. 5(a) has a satisfactory contrast and no adjustment of exposure time is required.

An example of an overexposed image is given as FIG. 6(a). The number of saturated pixels (DN=1023) is large, many more than any other value on the histogram. See FIG. 6(b). However, the search for the histogram edge begins at the maximum acceptable DN value. The algorithm immediately detects that the histogram is at a plateau and not at an edge. For the saturated pixels, the value input as the maximum acceptable value is reported for signal DN, but this is not a true value because the "true" value is unknown due to saturation. In this case, the contrast algorithm reports that the image is over-exposed and has an unsatisfactory contrast. This information is then passed to the second stage of the contrast maximization algorithm. Because the value characterizing the brightest cervical pixels is unknown, it is impossible to quantify an estimate of the optimal exposure time. Exposure times are preferably limited to a discrete set of acceptable values. For this reason, if an image is over-exposed, the exposure time is preferably decreased by approximately 5-10% and a new image is acquired. If this new exposure time is also too long, the algorithm again decreases the exposure time by approximately 5-10%.

Finally, an example of an under-exposed image is given as FIG. 7(a). Again there are a number of saturated pixels (DN=1023). See FIG. 7(b). However, nearly-empty histogram values extend far to the left of the saturation value. The histogram does not begin to curve upward until about DN=750. This is less than the minimum acceptable value of 800. As a result, the contrast of this image is unsatisfactory and it is designated as under-exposed.

In the case of under-exposure, the optimal exposure time can be estimated. Signal DN scales linearly with exposure time. A new exposure time is estimated using equation (3):

$$etimeNew = \frac{860 - zeroVal}{signalDN - zeroVal} \times etimeOld. \quad (3)$$

Here 860 is the goal for signal DN, determined as the average of the minimum acceptable value and the maximum acceptable value. To properly scale, the DN value corresponding to zero signal is subtracted from the goal value and the current value. The algorithm then selects the exposure time on the list which is closest to the new estimation.

Because a new exposure time can be quantifiably estimated in the case of under-exposure, it is preferable to under-expose rather than over-expose. Therefore, it is preferable to begin the assessment algorithms with an exposure time that is relatively short. The contrast maximization algorithm may determine the correct exposure time more quickly than if it has to step backward one-by-one to shorter times.

4. Composition Analysis
4.1 Problem Description

As stated earlier, the cervix should be centered within each image and should fill as much of the field of view as possible, without intersecting image borders. The purpose of the composition algorithm is to assess whether this is the case, and to provide feedback to the operator if it is not.

4.2 Algorithm Description

The ROI from the XP image is used as the input for this algorithm. First, the proximity of the ROI borders to the image borders is assessed. Preferably the ROI borders should be very close to the image borders without intersecting them. One way to express this is that the total ROI area should be approximately 90-99% of the total image area, with 95% being the optimal value. The invention, however, is operable if the ROI's area is within the range of 80-99% of the total image area. Thus, if the ROI's total area is less than approximately 90% of the image's area or greater than 100% of the image area, the BooleanBadBorders quality flag is set to true. Second, the center of the ROI is considered to be the midpoint of the maximum and minimum row and column positions and the ROI center's distance from the image center is calculated. The difference in distance between the ROI midpoint and image center has a maximum value threshold of 5%, which if exceeded, the Boolean BadCenter quality flag is set to true. Finally, the size of the ROI is compared to a minimum threshold of at least approximately 25% of the total area of the image in order to detect cases in which the cervix is obstructed in the camera field of view. If the size of the ROI is smaller than this minimum threshold, the Boolean BadArea quality flag is set to true. If any of the quality flags discussed above are true, then the composition is bad and the test(s) failed. However, if the ROI is centered, does not intersect the image borders, and is sufficiently large, then the output composition diagnostic message indicates that composition is good.

5. Status Assessment

Status assessment is another Boolean variable. It is assigned a value of good (true) if contrast maximization for XP and PP, and if composition for XP, are both satisfactory. Then the device is ready to collect high-resolution XP and PP images for the observation of clinically relevant features.

If status assessment is false, then some component has failed, and the adjustments recommended in the exposure time messages or composition quality flags should be employed. After these adjustments have been made, assessment algorithms should be repeated.

While the present invention has been particularly shown and described with reference to embodiments described in the detailed description and illustrated in the figures, it will be understood by one skilled in the art that various changes in detail may be effected therein without departing from the spirit and scope of the invention, as defined by the claims.

Accordingly, no limitations are to be implied or inferred except as explicitly set forth in the claims.

Industrial Applicability

This invention provides methods for tissue diagnosis systems to automatically analyze and adjust the quality of acquired images. It could be applicable to any imaging and analysis of a region of interest having a spectrum that differs from the background.

What is claimed is:

1. A method to provide automated quality feedback to imaging devices to achieve archive-quality standardized image data for use in electronic medical records and in computer-aided diagnostic (CAD) systems, comprising:
    collecting two versions of a raw image from live video during examination with a digital imager, wherein a first version of said raw image is created by illuminating a field of view with a light source having a first polarization orientation and viewing said field of view with a detector through a polarized filter having a second polarization orientation, wherein said first polarization orientation is substantially perpendicular to said second polarization orientation, to produce a cross-polarized image of said field of view, and wherein a second version of said raw image is produced when said second polarization orientation is substantially parallel to said first polarization orientation, to produce a parallel-polarized image of said field of view;
    wherein both of said images of said field of view are substantially co-registered, whereby they both have substantially the same borders, each border having a border length and a border width, defining an area within said borders, and a center;
    locating a region of interest on said cross-polarized image using an image classification algorithm, wherein said image classification algorithm comprises:
        discarding bad image pixels and determining a background mean spectrum,
        defining non-overlapping, spatially dispersed samples of substantially uniform size and spacing within said cross-polarized image, and calculating a luminance mean spectrum for each of said samples,
        discarding approximately 0-20% of the brightest of said samples and approximately 10-50% of the darkest of said samples, whereby remaining samples are left,
        averaging the luminance mean spectra of said remaining samples to determine said a target luminance spectrum, and
        determining said region of interest's size by ascertaining the portion of said cross-polarized image that substantially matches said target luminance spectrum;
    performing contrast maximization by signal assessment and exposure time adjustment to said cross-polarized image and said parallel-polarized image;
    applying composition analysis to said cross-polarized image to ensure said region of interest is centered within said cross-polarized image;
    determining an assessment status of said contrast maximization and said composition analysis, wherein said assessment status is reported as either a Boolean variable of good or bad;
    if said status is bad, repeating said collecting of two versions of a raw image, said locating a region of interest, said performing contrast maximization and said composition analysis; and
    if said status is good, collecting a high-resolution cross-polarized still image and a high-resolution parallel-polarized still image.

2. A method to provide automated quality feedback to imaging devices to achieve archive-quality standardized image data for use in electronic medical records and in computer-aided diagnostic (CAD) systems, comprising:
    collecting two versions of a raw image from live video during examination with a digital imager, wherein a first version of said raw image is created by illuminating a field of view with a light source having a first polarization orientation and viewing said field of view with a detector through a polarized filter having a second polarization orientation, wherein said first polarization orientation is substantially perpendicular to said second polarization orientation, to produce a cross-polarized image of said field of view, and wherein a second version of said raw image is obtained by placing a polarized filter at a location selected from the group consisting of said light source and said detector, to produce a singly-polarized image of said field of view;
    wherein both of said images of said field of view are substantially co-registered, whereby they both have substantially the same borders, each border having a border length and a border width, defining an area within said borders, and a center;
    locating a region of interest on said cross-polarized image using an image classification algorithm, wherein said image classification algorithm comprises:
        discarding bad image pixels and determining a background mean spectrum,
        defining non-overlapping, spatially dispersed samples of substantially uniform size and spacing within said cross-polarized image, and calculating a luminance mean spectrum for each of said samples,
        discarding approximately 0-20% of the brightest of said samples and approximately 10-50% of the darkest of said samples, whereby remaining samples are left,
        averaging the luminance mean spectra of the said remaining samples to determine a target luminance spectrum, and
        determining said region of interest's size by ascertaining the portion of said cross-polarized image that substantially matches said target luminance spectrum;
    performing contrast maximization by signal assessment and exposure time adjustment to said cross-polarized image and said singly-polarized image;
    applying composition analysis to said cross-polarized image to ensure said region of interest is centered within said cross-polarized image;
    determining an assessment status of said contrast maximization and said composition analysis, wherein said assessment status is reported as either a Boolean variable of good or bad;
    if said status is bad, repeating said collecting of two versions of a raw image, said locating a region of interest, said performing contrast maximization and said composition analysis; and
    if said status is good, collecting a high-resolution cross-polarized still image and a high-resolution singly-polarized still image.

3. A method according to claim 1 or 2, wherein said image classification algorithm determines said region of interest's size using a spectral match filter to estimate a spectral angle between said spectra of the remaining samples and said target spectrum, and wherein said cross-polarized image substantially matches said target spectrum when said spectral angle is less than approximately 65-85 degrees.

4. A method according to claim 1 or 2, wherein said image classification algorithm is performed using spatially dispersed samples of spectra that comprise a plurality of boxes dispersed near said center of said cross-polarized image, each of said boxes having a box length and a box width, and wherein said box lengths are approximately 10-30% of said border length of said cross-polarized image, and wherein said boxes cover approximately 20-60% of said area within said borders of said cross-polarized image.

5. A method according to claim 1 or 2, wherein said image classification algorithm is performed by discarding approximately 10-15% of the brightest and approximately 20-40% of the darkest samples of spectra.

6. A method according to claim 1 or 2, said image classification algorithm is performed by discarding 12% of the brightest and 30% of the darkest sample spectra.

7. A method according to claim 1, wherein said contrast maximization step is performed by adjusting exposure time for said region of interest to generate brightest pixels in said cross-polarized image and said in said parallel-polarized image whose brightness is determined by a digital number, and wherein said brightest pixels have a digital number that falls within a desired range to produce a satisfactory contrast, and wherein the minimum value of said desired range is approximately 80% of the maximum digital number value for said cross-polarized image and is 80% of the maximum digital number value for said parallel-polarized image, and wherein the maximum value of said desired range preferably corresponds to approximately 90% of the maximum digital number value for said cross-polarized image and is approximately 90% of the maximum digital number value for said parallel-polarized image.

8. A method according to claim 2, wherein said contrast maximization step is performed by adjusting exposure time for said region of interest to generate brightest pixels in said cross-polarized image and in said singly-polarized image whose brightness is determined by a digital number, and wherein said brightest pixels have a digital number that falls within a desired range to produce a satisfactory contrast, and wherein the minimum value of said desired range is approximately 80% of the maximum digital number value for said cross-polarized image and is 80% of the maximum digital number value for said singly-polarized image, and wherein the maximum value of said desired range preferably corresponds to approximately 90% of the maximum digital number value for said cross-polarized image and is approximately 90% of the maximum digital number value for said singly-polarized image.

9. A method according to claim 1 or 2, wherein said composition analysis step is performed by assessing within said cross-polarized image the proximity of the borders of said region of interest to said borders of said cross-polarized image, determining the proximity of the center of the said region of interest to said center of said cross-polarized image, and calculating the size of said region of interest, and reporting a composition diagnostic message.

10. A method according to claim 9, wherein said composition diagnostic message is reported as satisfactory when said region of interest is centered within said cross-polarized image, is contained within said cross-polarized image borders, and said size of said region of interest is at least approximately 25% of the total area of said cross-polarized image.

11. A method according to claim 1 or 2, wherein said Boolean variable of good applies only when said contrast maximization and said composition analysis are satisfactory.

12. A method according to claim 1 or 2, wherein said Boolean variable of bad applies when either said contrast maximization or said composition analysis are unsatisfactory or when both contrast maximization and said composition analysis are unsatisfactory.

13. A method to provide automated quality feedback to imaging devices to achieve archive-quality standardized image data for use in electronic medical records and in computer-aided diagnostic (CAD) systems, comprising:
collecting two versions of a raw image from live video during examination with a digital imager, wherein a first version of said raw image is created by illuminating a field of view with a light source having a first polarization orientation and viewing said field of view with a detector through a polarized filter having a second polarization orientation, wherein said first polarization orientation is substantially perpendicular to said second polarization orientation, to produce a cross-polarized image of said field of view, and wherein a second version of said raw image is produced when said second polarization orientation is substantially parallel to said first polarization orientation, to produce a parallel-polarized image of said field of view;
wherein both of said images of said field of view are substantially co-registered, whereby they both have substantially the same borders, each border having a border length and a border width, defining an area within said borders, and a center;
locating a region of interest on said cross-polarized image using an image classification algorithm, wherein said image classification algorithm comprises:
discarding bad image pixels and determining a background mean spectrum,
defining non-overlapping, spatially dispersed samples of substantially uniform size and spacing within said cross-polarized image, and calculating a luminance mean spectrum for each of said samples,
discarding approximately 0-20% of the brightest of said samples and approximately 10-50% of the darkest of said samples, whereby remaining samples are left,
averaging the luminance mean spectra of the said remaining samples to determine a target luminance spectrum, and
determining said region of interest's size by ascertaining the portion of said cross-polarized image that substantially matches said target luminance spectrum;
performing contrast maximization by signal assessment and exposure time adjustment to said cross-polarized image and said parallel-polarized image by adjusting exposure time for said region of interest to generate brightest pixels in said cross-polarized image and in said parallel-polarized image whose brightness is determined by a digital number, and wherein said brightest pixels have a digital number that falls within a desired range to produce a satisfactory contrast, and wherein the minimum value of said desired range is approximately 80% of the maximum digital number value for said cross-polarized image and is 80% of the maximum digital number value for said parallel-polarized image, and wherein the maximum value of said desired range preferably corresponds to approximately 90% of the maximum digital number value for said cross-polarized image and is approximately 90% of the maximum digital number value for said parallel-polarized image;
applying composition analysis to said cross-polarized image by assessing within said cross-polarized image the proximity of the borders of said region of interest to said borders of said cross-polarized image, determining the proximity of the center of the said region of interest to said center of said cross-polarized image, and calculating the size of said region of interest, and reporting a composition diagnostic message, wherein said composition diagnostic message is reported as satisfactory when said region of interest is centered within said cross-polarized image, is contained within said cross-polarized image borders, and said size of said region of interest is at least approximately 25% of the total area of said cross-polarized image;

determining an assessment status of said contrast maximization and said composition analysis, wherein said assessment status is reported as either a Boolean variable of good or bad, and wherein said Boolean variable of good applies only when said contrast maximization and said composition analysis are satisfactory, and wherein said Boolean variable of bad applies when either said contrast maximization or said composition analysis are unsatisfactory or when both contrast maximization and said composition analysis are unsatisfactory;

if said status is bad, repeating said collecting of two versions of a raw image, said locating a region of interest, said performing contrast maximization and said composition analysis; and if said status is good, collecting a high-resolution cross-polarized still image and a high-resolution parallel-polarized still image.

14. A method to provide automated quality feedback to imaging devices to achieve archive-quality standardized image data for use in electronic medical records and in computer-aided diagnostic (CAD) systems, comprising:

collecting two versions of a raw image from live video during examination with a digital imager, wherein a first version of said raw image is created by illuminating a field of view with a light source having a first polarization orientation and viewing said field of view with a detector through a polarized filter having a second polarization orientation, wherein said first polarization orientation is substantially perpendicular to said second polarization orientation, to produce a cross-polarized image of said field of view, and wherein a second version of said raw image is obtained by placing a polarized filter at at-a location selected from the group consisting of said light source and said detector, to produce a singly-polarized image of said field of view;

wherein both of said images of said field of view are substantially co-registered, whereby they both have substantially the same borders, each border having a border length and a border width, defining an area within said borders, and a center;

locating a region of interest on said cross-polarized image using an image classification algorithm, wherein said image classification algorithm comprises:

discarding bad image pixels and determining a background mean spectrum, defining non-overlapping, spatially dispersed samples of substantially uniform size and spacing within said cross-polarized image, and calculating a luminance mean spectrum for each of said samples, discarding approximately 0-20% of the brightest of said samples and approximately 10-50% of the darkest of said samples, whereby remaining samples are left, averaging the luminance mean spectra of said remaining samples to determine a target luminance spectrum, and determining said region of interest's size by ascertaining the portion of said cross-polarized image that substantially matches said target luminance spectrum;

performing contrast maximization by signal assessment and exposure time adjustment to said cross-polarized image and said singly-polarized image by adjusting exposure time for said region of interest to generate brightest pixels in said cross-polarized image and in said singly-polarized image whose brightness is determined by a digital number, and wherein said brightest pixels have a digital number that falls within a desired range to produce a satisfactory contrast, and wherein the minimum value of said desired range is approximately 80% of the maximum digital number value for said cross-polarized image and is 80% of the maximum digital number value for said singly-polarized image, and wherein the maximum value of said desired range preferably corresponds to approximately 90% of the maximum digital number value for said cross-polarized image and is approximately 90% of the maximum digital number value for said singly-polarized image;

applying composition analysis to said cross-polarized image by assessing within said cross-polarized image the proximity of the borders of said region of interest to said borders of said cross-polarized image, determining the proximity of the center of the said region of interest to said center of said cross-polarized image, and calculating the size of said region of interest, and reporting a composition diagnostic message, wherein said composition diagnostic message is reported as satisfactory when said region of interest is centered within said cross-polarized image, is contained within said cross-polarized image borders, and said size of said region of interest is at least approximately 25% of the total area of said cross-polarized image;

determining an assessment status of said contrast maximization and said composition analysis, wherein said assessment status is reported as either a Boolean variable of good or bad, and wherein said Boolean variable of good applies only when said contrast maximization and said composition analysis are satisfactory, and wherein said Boolean variable of bad applies when either said contrast maximization or said composition analysis are unsatisfactory or when both contrast maximization and said composition analysis are unsatisfactory;

if said status is bad, repeating said collecting of two versions of a raw image, said locating a region of interest, said performing contrast maximization and said composition analysis; and if said status is good, collecting a high-resolution cross-polarized still image and a high-resolution singly-polarized still image.

* * * * *